United States Patent
Rust et al.

(10) Patent No.: US 7,038,058 B2
(45) Date of Patent: May 2, 2006

(54) CONTINUOUS PREPARATION OF SUBSTITUTED OXAZOLES

(75) Inventors: Harald Rust, Neustadt (DE); Kirsten Burkart, Ludwigshafen (DE); Tillmann Faust, Weisenheim (DE); Jochem Henkelmann, Mannheim (DE); Alois Kindler, Gruenstadt (DE); Christian Knoll, Neuhofen (DE); Andre Mohry, Wesseling (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 115 days.

(21) Appl. No.: 10/726,183

(22) Filed: Dec. 3, 2003

(65) Prior Publication Data

US 2004/0110961 A1 Jun. 10, 2004

Related U.S. Application Data

(60) Division of application No. 10/300,629, filed on Nov. 21, 2002, now Pat. No. 6,713,630, which is a continuation-in-part of application No. 10/207,894, filed on Jul. 31, 2002, now abandoned.

(30) Foreign Application Priority Data

Aug. 3, 2001 (DE) ............... 101 37 627
Mar. 5, 2002 (DE) ............... 102 09 447

(51) Int. Cl.
C07D 263/30 (2006.01)

(52) U.S. Cl. .............. 548/228; 546/290; 546/301

(58) Field of Classification Search .......... 548/215, 548/225, 228; 546/290, 301
See application file for complete search history.

(56) References Cited

U.S. PATENT DOCUMENTS

| 3,227,721 | A | 1/1966 | Pfister | |
|---|---|---|---|---|
| 6,713,630 | B1* | 3/2004 | Rust et al. | 548/228 |
| 6,900,332 | B1* | 5/2005 | Rust et al. | 548/228 |

FOREIGN PATENT DOCUMENTS

| DE | 30 29231 | 3/1982 |
|---|---|---|
| JP | 45 11906 | 4/1970 |

OTHER PUBLICATIONS

Chem. Reviews, 1975, vol. 75, No. 4, Turchi et al.
Derwent Abst. JP7 9020-493.
Chem.Ber. 1969, 93, 239-248.
Chem.Ber. 1975, 1580-1590.
J. Heterocyclic Chem. 1988, 17, 705.
Ullmanns Enc. Ind. Chem. 1996, vol. A27, 533-537.
T.W. Greene, Protective Groups in Organic Synthesis, 1981, 14-71, John Wiley & Sons, NewYork.
Protecting Groups, Georg Thieme Verlag Stgt. 1994, 21-94.
Angew. Chem. 1965, 77, 492-504.
Khimiko-Farmatsevticheskii Zhurnal. vol. 12, No. 12. 102-106, Dec. 1978, Itov et al.
Khimiko-Farmatsevticheskii Zhurnal, 1988, 7, 856-860, Mishchenlo et al.
Bull. Chem. Soc. , Japan, 1971, 44, 1407-1410, Maeda et al.
Chem. Ber. 106, 3382-3390 (1973) XP-001105793, Schoellkopf et al.

* cited by examiner

*Primary Examiner*—Golam M. M. Shameem
(74) *Attorney, Agent, or Firm*—Novak Druce Deluca & Quigg, LLP; Jason D. Voight

(57) ABSTRACT

The present invention relates to a process for continuously preparing 5-alkoxy-substituted oxazoles, in particular for continuously preparing 4-methyl-5-alkoxy-substituted oxazoles and also a process for preparing pyridoxine derivatives.

6 Claims, 1 Drawing Sheet

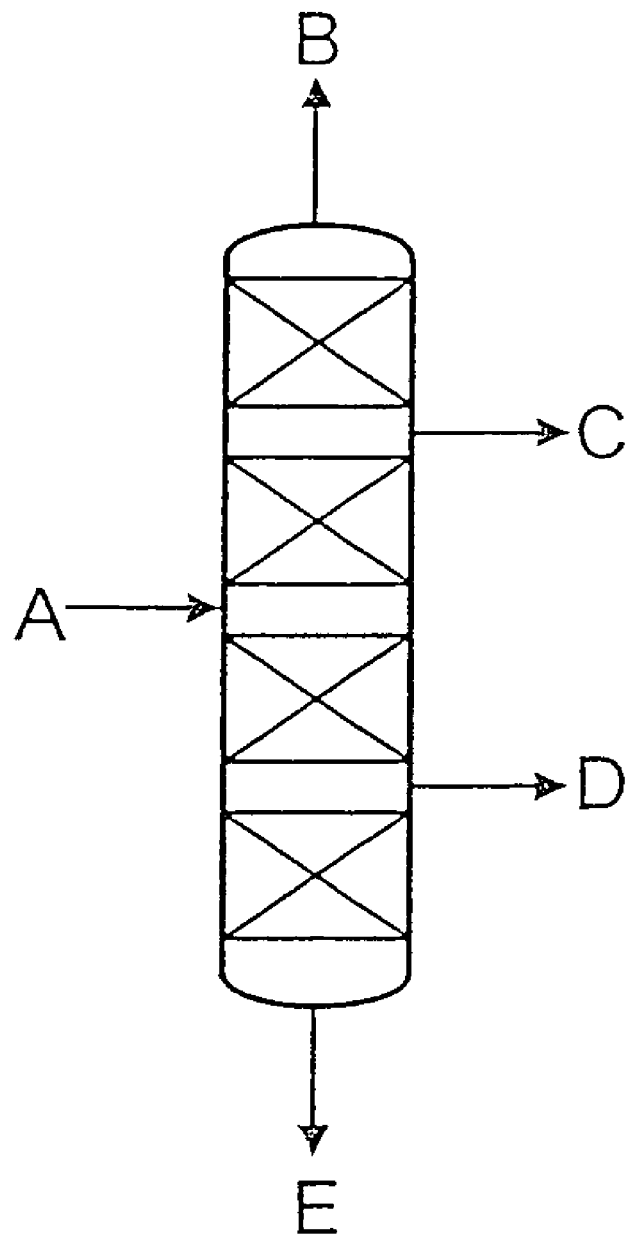

CONTINUOUS PREPARATION OF SUBSTITUTED OXAZOLES

This is a divisional application of U.S. Ser. No. 10/300,629 filed Nov. 21, 2002, now U.S. Pat. No. 6,713,630 which is a continuation in part of U.S. Ser. No. 10/207,894, filed Jul. 31, 2002 and now abandoned.

The present invention relates to a process for continuously preparing 5-alkoxy-substituted oxazoles, in particular for continuously preparing 4-methyl-5-alkoxy-substituted oxazoles and also a process for preparing pyridoxine derivatives.

5-Alkoxy-substituted oxazoles are valuable synthetic building blocks in organic chemistry. 4-Methyl-5-alkoxy-substituted oxazoles have particular significance as important precursors for the synthesis and industrial production of vitamin $B_6$ (Turchi et al., Chem. Rev. 1975, 75, 416).

A process which is economically viable and is operable on a large scale for preparing 5-alkoxy-substituted oxazoles, in particular 4-methyl-5-alkoxy-substituted oxazoles, is therefore of great significance.

It is known that α-isocyanoalkanoate esters can be converted batchwise by thermal isomerization into the corresponding 5-alkoxy-substituted oxazoles.

Itov et al., Khimiko-Farmatsevticheskii Zhurnal, 1978, 12, 102 to 106 and Mishchenlo et al., Khimiko-Farmatsevticheskii Zhurnal, 1988, 7, 856 to 860 describe a batchwise thermal cyclization of α-isocyanopropionate esters to give the corresponding 4-methyl-5-alkoxy-substituted oxazoles at 135° C. The yields of 4-methyl-5-alkoxy-substituted oxazoles achieved by the use of various solvents are from 4 to 36%. The process has the disadvantage of low selectivity and thus the disadvantage that large amounts of by-products are formed. The most frequent by-products of this reaction are the unconverted reactant (yield: 33 to 55%) and also the rearranged α-cyanopropionate ester (yield: 1 to 39%).

Maeda et al., Bull. Chem. Soc. Japan, 1971, 44, 1407 to 1410 disclose a batchwise thermal cyclization of various α-isocyanocarboxylate esters to give the corresponding 5-alkoxy-substituted oxazoles at temperatures of from 150 to 180° C. Depending on the substituents, yields of from 5.1 to 28.2% are achieved.

JP 54-20493 describes a batchwise process for preparing 4-methyl-5-alkoxy-substituted oxazoles by thermally cyclizing α-isocyanopropionate esters at temperatures of 155 and 170° C. in the presence of a tertiary amine. Although improved selectivities for the desired oxazoles are achieved (from 34 to 91.5%), the low conversion (from 11.1 to 49.4%) leads to yields which are still unsatisfactory.

All of the prior art processes have the disadvantage of low conversions and low selectivities and thus low yields of 5-alkoxy-substituted oxazoles. Owing to the batchwise processing method, the prior art processes only have low space-time yields.

It is an object of the present invention to provide a further process for preparing 5-alkoxy-substituted oxazoles which has advantageous characteristics, does not have the disadvantages of the prior art and delivers the 5-alkoxy-substituted oxazoles in high yields and high space-time yields.

We have found that this object is achieved by a process for continuously preparing 5-alkoxy-substituted oxazoles of the formula I,

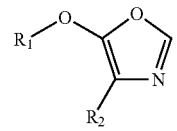

where
$R_1$ is an unsubstituted or substituted $C_1$–$C_6$-alkyl radical and
$R_2$ is hydrogen or an unsubstituted or substituted $C_1$–$C_6$-alkyl radical,
which comprises
converting continuously added α-isocyanoalkanoate esters of the formula II

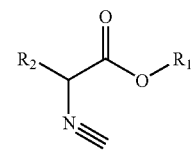

in the presence of continuously added assistants at temperatures above 80° C.
in a reactor to the 5-alkoxy-substituted oxazoles of the formula I and continuously removing the reaction products from the reactor.

The $C_1$–$C_6$-alkyl radicals $R_1$ and $R_2$ are each independently branched or unbranched, substituted or unsubstituted $C_1$–$C_6$-alkyl radicals, for example, substituted or unsubstituted methyl, ethyl, propyl, 1-methylethyl, n-butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl or 2-ethylbutyl.

The nature of the substituents is not critical. The $C_1$–$C_6$-alkyl radicals may, depending on the possibility of free bonds, contain up to 6 substituents, preferably selected from the group consisting of aryl, hydroxyaryl, —$NO_2$, —$NH_2$, —OH, —CN, —COOH, or halogen, in particular F or Cl.

In a preferred embodiment, the $C_1$–$C_6$-alkyl radicals $R_1$ and $R_2$ are unsubstituted.

Preferred $R_1$ radicals include $C_1$–$C_4$-alkyl radicals, for example, methyl, ethyl, isopropyl, n-propyl, n-butyl, sec-butyl or tert-butyl, more preferably n-butyl.

Preferred $R_2$ radicals include hydrogen and $C_1$–$C_4$-alkyl radicals, for example, methyl, ethyl, isopropyl, n-propyl, n-butyl, sec-butyl or tert-butyl, more preferably methyl.

Preference is given to the combination of the preferred radicals for $R_1$ and $R_2$, and particular preference to the combination of $R_1$=n-butyl and $R_2$=methyl.

In a particularly preferred embodiment of the process according to the invention, n-butyl α-isocyanopropionate is accordingly converted into 4-methyl-5-n-butoxyoxazole.

The α-isocyanoalkanoate esters of the formula II used in the process according to the invention may be of any desired purity.

The α-isocyanoalkanoate esters of the formula II are prepared in a manner known per se from the corresponding formamido esters of the formula V

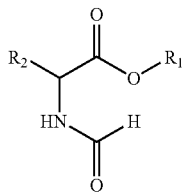

by reacting them with phosphorus oxychloride or phosgene in the presence of bases. Common synthetic methods are described in Itov et al., Khimiko-Farmatsevticheskii Zhurnal, 1978, 12, 102–106; Maeda et al., Bull. Chem. Soc. Japan, 1971, 44, 1407–1410; Ugi et al., Chem. Ber. 1961, 94, 2814; Chem. Ber. 1960, 93, 239–248, Angew. Chem. 1965, 77, 492–504, Chem. Ber. 1975, 1580–1590, DE 30 29 231 A1 and J. Heterocyclic Chemistry 1988, 17, 705.

For the purposes of the present invention, assistants are chemical compounds, preferably chemical compounds which accelerate the cyclization reaction or shift the thermodynamic equilibrium in the direction of the desired product. Preferred assistants include cyclizing assistants selected from the group consisting of bases, alcohols and esters.

For the purposes of the present invention, bases are compounds having Brønsted base properties. Preferred bases include tertiary amines, for example, triethylamine, triisopropylamine, tri-n-butylamine, dimethylcyclohexylamine, tris(2-ethylhexyl)amine, N-methylpyrrolidone, N,N,N'N'-tetramethyl-1,3-propanediamine, N,N-diethylaniline or N,N-dibutylaniline. Particular preference is given to the use of tri-n-butylamine as base.

Preferred alcohols are substituted or unsubstituted $C_1$–$C_6$-alkanols, for example, methanol, ethanol, n-propanol, isopropanol, n-butanol, sec-butanol, tert-butanol, n-pentanol or n-hexanol. Particular preference is given to the use of n-butanol as alcohol.

Preferred esters include substituted or unsubstituted $C_1$–$C_6$-alkyl $C_1$–$C_6$-alkanoates, for example, methyl acetate, ethyl acetate, propyl acetate, n-butyl acetate, tert-butyl acetate, hexyl acetate, methyl propionate, ethyl propionate, propyl propionate, n-butyl propionate, tert-butyl propionate, hexyl propionate, ethyl butanoate, ethyl butanoate, propyl butanoate, n-butyl butanoate, tert-butyl butanoate, or hexyl butanoate. Particular preference is given to the use of n-butyl propionate as an ester.

The assistants may be used as individual compounds or in the form of mixtures. Preference is given to using the assistants as individual compounds.

Below 80° C., no noticeable thermal cyclization takes place. The temperature of the conversion according to the invention is accordingly at least 80° C.

In a preferred embodiment, the process according to the invention is operated at temperatures of from 100 to 200° C., more preferably at temperatures of from 120 to 170° C., most preferably at temperatures of from 130 to 170° C.

The molar ratio of assistant to α-isocyanoalkanoate ester of the formula II is not critical and is preferably from 10:1 to 0.05:1.

In the process according to the invention, the α-isocyanoalkanoate esters of the formula II and the assistants are either added as a mixture or separately and continuously to a reactor, the α-isocyanoalkanoate esters of the formula II are converted in the reactor to the 5-alkoxy-substituted oxazoles of the formula I and then the reaction products are withdrawn continuously from the reactor.

In principle, useful reactors include all reactors which facilitate a continuous method.

In a preferred embodiment of the process according to the invention, the reactor used is a tubular reactor. This continuously operated reactor preferably has no backmixing.

Accordingly, preference is given to a tubular reactor having a Bodenstein number greater than or equal to 50, which is determined in a manner known per se, for example, as described in Fitzer-Fritz, Technische Chemie, 3rd edition, Springer-Verlag, pages 288 ff.

Preference is given to the tubular reactor additionally having a theoretical tank number greater than or equal to 50.

The pressure in the tubular reactor and the residence time are not critical, although the reactor is preferably operated with pressure control and the residence time controlled by the metering in of the reactants.

The pressure in the tubular reactor is preferably at least 2 bar, more preferably from 3 to 9 bar, particularly preferably from 4 to 7 bar, in particular 5 bar.

The residence time is preferably from 1 to 8 hours, more preferably from 2 to 6 hours, particularly preferably from 3 to 5 hours, in particular 4 hours.

In a particularly preferred embodiment of this process variant using a tubular reactor, the compounds of the formula II are advantageously only partially converted in the tubular reactor. The partial conversion is preferably from 40 to 70%, more preferably from 50 to 60%, in particular 54%.

In this preferred embodiment using a tubular reactor, it is particularly advantageous to feed the effluent of the tubular reactor into a continuously operated column and to continuously and distillatively separate it in the column into a low-boiling fraction comprising the compounds of the formula I and a high-boiling fraction comprising unconverted compounds of the formula II and assistants.

Preferred columns are the continuously operated reaction columns described below.

In this embodiment with the column attached downstream, a further conversion may be effected in the column attached downstream, as described below.

In a further preferred embodiment of this variant using the tubular reactor having a column attached downstream, the low-boiling fraction discharged from the column comprising unconverted compounds of the formula II and assistants is recycled into the reaction. This achieves a conversion of the compounds of the formula II of the overal process of 100%.

Another preferred embodiment of the continuous process according to the invention can be particularly advantageously carried out by removing the 5-alkoxy-substituted oxazoles of the formula I from the reaction mixture during the conversion in the reactor, i.e. simultaneously with the conversion. This removal is preferably likewise effected continuously.

There are many reactor designs which are useful for this preferred embodiment of the process according to the invention. Preferred reactors should have the property of facilitating a continuous conversion while simultaneously removing a reaction product.

Examples of useful reactors include stills having emplaced columns, extraction columns, bubble cap tray columns, membrane reactors, Lord reactors or reaction columns.

As is known to those skilled in the art, the term column, unless otherwise stated, refers to a column construction having a liquid phase.

Accordingly, an emplaced column refers only to a column construction without a liquid phase.

Reaction columns are preferably columns whose internals have a hold-up, for example, columns having trays, beds, structured packings or random packings.

In a particularly preferred embodiment of the process according to the invention, the reaction is carried out in a reaction column as reactor.

The reaction columns may be configured as desired by the construction and the internals. Particular preference is given to the use of a dividing wall column as the reaction column.

A reaction column which can be configured in highly varied ways has the characteristic of being a reactor which can simultaneously facilitate a conversion of reactants and the removal by rectification of the 5-alkoxy-substituted oxazoles of the formula I from the reaction mixture.

In this preferred embodiment employing a reaction column, it is also advantageous to set the rectification parameters in such a way that A the α-isocyanoalkanoate esters of the formula II are converted to the 5-alkoxy-substituted oxazoles of the formula I on the internals and, if present, in the liquid phase of the reaction column, B the 5-alkoxy-substituted oxazoles of the formula I resulting from the conversion are continuously removed with the top stream or sidestream of the reaction column and C the assistant and any high-boilers resulting from the conversion are removed continuously and independently of each other with the bottom stream or sidestream of the reaction column.

Depending on the design of the reaction column and the reactants used, this is achieved by different settings of the rectification parameters. Examples of suitable rectification parameters include temperature, pressure, reflux ratio in the column, configuration of the column and its internals, heat transfer and residence time, in particular in the liquid phase, and energy introduction, each of which may be optimized through routine experiments by those skilled in the art in such a way that the characteristics A, B and C are achieved.

In feature C, the assistants may in particular also be removed from the high-boilers in a second sidestream.

For the purposes of the present invention, a sidestream is the continuous discharge of a substance via a sidestream takeoff of the column.

In the process according to the invention, the pressure at the top of the column is also set in such a way that the temperature in the liquid phase and on the internals is at least 80° C., preferably from 100 to 200° C., more preferably from 120 to 170° C.

Typically, the top pressure of the column is set to from 5 to 800 mbar, in such a way that the bottom pressure resulting from the column type used and the tanks of any column internals used is typically from 5 mbar to atmospheric pressure.

The residence time in the reaction column is typically from 10 minutes to 7 hours, preferably from 30 minutes to 4 hours.

It is possible that the 5-alkoxy-substituted oxazoles of the formula I form an azeotropic mixture with the assistants used so that the 5-alkoxy-substituted oxazoles of the formula I are removed via the top stream as an azeotropic mixture.

In this case, it is advantageous to set the top pressure and therefore also automatically the bottom pressure in the column in such a way that, depending on the 5-alkoxy-substituted oxazole of the formula I prepared and the assistant used, the fraction of assistant in the azeotrope in the top stream is as low as possible.

The assistant is removed from the top stream azeotrope in this case by a manner known per se, for example by a subsequent second rectification using a different pressure (two-pressure distillation).

For example, 4-methyl-5-n-butoxyoxazole prepared by the process according to the invention forms an azeotrope with the base tri-n-butylamine. When the top pressure is adjusted to 100 mbar, the azeotrope in the topstream is composed of 91% by weight of 4-methyl-5-n-butoxyoxazole and 9% by weight of tri-n-butylamine.

In this case, the tri-n-butylamine can be removed from the topstream azeotrope, for example, by a subsequent second rectification of the top pressure of 10 mbar.

The process according to the invention may be carried out in the presence or absence of solvents. In a preferred embodiment, the continuous process according to the invention is carried out without solvents.

In a further preferred embodiment, the process according to the invention is carried out in the presence of an inert solvent. Preferred inert solvents include nonpolar and polar aprotic solvents such as toluene, xylene or chlorobenzene, dichloromethane, dichloroethane, dichlorobenzene, ethylene carbonate, propylene carbonate, and in particular chlorobenzene.

When a solvent is used, the solvent may be added continuously to the column, for example, in a mixture with the assistant and the α-isocyanoalkanoate esters of the formula II or each individual component may be added separately.

When an inert solvent is used in the process according to the invention, preference is given to setting the rectification parameters in such a way that A the α-isocyanoalkanoate esters of the formula II are converted to the 5-alkoxy-substituted oxazoles of the formula I on the internals and, if present, in the liquid phase of the reaction column, B1 when the solvent has a higher boiling point than the 5-alkoxy-substituted oxazoles of the formula I resulting from the conversion, the 5-alkoxy-substituted oxazoles of the formula I are continuously removed with the top stream and the solvent is continuously removed via the sidestream or bottom stream of the reaction column, B2 when the solvent has a lower boiling point than the 5-alkoxy-substituted oxazoles of the formula I resulting from the conversion, the 5-alkoxy-substituted oxazoles of the formula I are continuously removed with a sidestream and the solvent is continuously removed with the top stream of the reaction column and C the assistant and any high-boilers resulting from the conversion are removed continuously and independently of each other with the top stream or sidestream of the reaction column.

The internals used in the reaction column may be of any design, for example, column trays, beds, random packings or structured packings.

Particularly advantageous column trays facilitate a long residence time of the liquid, and the residence time on the internals of the reaction column is preferably at least 30 min.

Examples of preferred column trays include valve trays, preferably bubble cap trays, or related designs, for example, tunnel cap trays, Lord reactors and other internals or Thormann trays.

Examples of preferred structured packings include structured packings of the Mellapack® (Sulzer), BY® (Sulzer), B1® (Montz) or A3® (Montz) types or packings having comparable designs.

The process according to the invention has the following advantages over the prior art:

The process according to the invention achieves selectivities of over 95% based on the α-isocyanoalkanoate esters of the formula II used.

The conversion is almost 100%, so that the yields of 5-alkoxy-substituted oxazoles of the formula I is over 95%, based on the α-isocyanoalkanoate esters of the formula II used.

A further advantage of the process is the continuous processing method. The space-time yield is distinctly greater than the prior art processes.

The process according to the invention provides a novel and advantageous contributory synthetic step in the process for preparing pyridoxine derivatives of the formula IX,

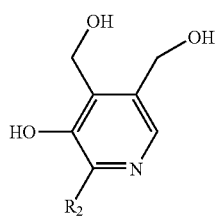

in particular for preparing pyridoxine (vitamin $B_6$; formula IX, $R_2$=methyl).

The invention accordingly also relates to a process for preparing pyridoxine derivatives of the formula IX which comprises converting amino acids of the formula III

III to amino esters of the formula IV,

IV converting the latter into formamido esters of the formula V,

V converting the latter into α-isocyanoalkanoate esters of the formula II,

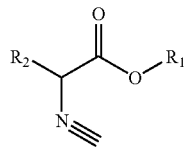

converting the latter in a continuous process step according to the invention
in the presence of assistants
at temperatures above 80° C.
to 5-alkoxy-substituted oxazoles of the formula I

I reacting the latter with protected diols of the formula VI,

VI where
$R_3$ and $R_4$ independently or $R_3$ and $R_4$ together are a protecting group of the hydroxy function
to give the Diels-Alder adducts of the formula VII,

VII and converting the latter by acid treatment and detachment of the protecting group to the pyridoxine derivatives of the formula IX.

The overall process is, apart from the novel, advantageous contributory step according to the invention for the continuous conversion of α-isocyanoalkanoate esters of the formula II to 5-alkoxy-substituted oxazoles of the formula I, disclosed by Ullmann's Encyclopedia of Industrial Chemistry 1996, Vol. A 27, pages 533 to 537.

The starting materials for the overall synthesis are inexpensive amino acids of the formula III, preferably alanine ($R_2$=methyl). These are converted in a manner known per se, for example by acid-catalyzed esterification with the alcohols $R_1$—OH, preferably n-butanol to amino esters of the formula IV. This esterification may also be cheaper than other methods, for example, by activating the acid function and base-catalyzed esterification. Further methods are described in U.S. Pat. No. 3,227,721.

The amino esters of the formula IV are converted in a manner known per se, for example as described in U.S. Pat. No. 3,227,721, to the formamido esters of the formula V.

The formamido esters of the formula V are then converted in a manner known per se, as described above, to the α-isocyanoalkanoate esters of the formula II.

The α-isocyanoalkanoate esters of the formula II are continuously converted, as described above, by the process according to the invention to the 5-alkoxy-substituted oxazoles of the formula I.

In the preferred overall process, this contributory step is carried out in the preferred embodiments, as described above.

The 5-alkoxy-substituted oxazoles of the formula I are then reacted with protected diols of the formula VI to give the Diels-Alder adducts of the formula VII.

This contributory step may be downstream of the process according to the invention, but may also be carried out by continuously adding the protected diols of the formula VI to the reactor of the process according to the invention simultaneously with the conversion of the α-isocyanoalkanoate esters of the formula II to the 5-alkoxy-substituted oxazoles of the formula I. The addition may be carried out either in a mixture with the α-isocyanoalkanoate esters of the formula II, the assistant and any solvent or as a separate component. In this case, the 5-alkoxy-substituted oxazole products are withdrawn directly in the form of their Diels-Alder adducts via the bottom discharge of the column.

The $R_3$ and $R_4$ radicals are each independently a protecting group, preferably an acid-labile protecting group, of the hydroxyl function.

In principle, any acid-labile protecting group may be used. Preferred acid-labile protecting groups are the acid-labile protecting groups for hydroxyl groups known from the literature (T. W. Greene, Protective Groups in Organic Synthesis, John Wiley & Sons New York, 1981, pages 14–71; P. J. Kocienski, Protecting Groups, Georg Thieme Verlag Stuttgart, 1994, pages 21–94).

In a preferred embodiment, the $R_3$ and $R_4$ radicals together may also form an acid-labile protecting group of both hydroxyl functions. The two hydroxyl functions preferably form a cyclic acetal with ketones or aldehydes, for example, acetone or isobutyraldehyde.

Subsequent acid treatments of the Diels-Alder adducts of the formula VII with elimination of the alcohol $R_1$—OH results in aromatization to give the pyridoxine skeleton. The cleavage of the acid-labile protecting group(s) which is generally carried out by aqueous acid treatment delivers the pyridoxine derivatives of the formula IX, in particular pyridoxine (vitamin B6, $R_2$=methyl).

The alcohol $R_1$—OH and the protecting groups $R_3$ and $R_4$ may be recovered and reused in the overall process.

The use of the novel advantageous contributory step according to the invention in the overall process leads to an increase in the overall yield.

The following examples illustrate the invention:

EXAMPLE 1

Continuous Preparation of 4-methyl-5-n-butoxyoxazole in a Dividing Wall Column

A continuously operated dividing wall column (4.8 m×64 mm) packed with 3×3 mm of $V_2A$ Raschig rings and a dividing wall of height 2.4 m having 60 theoretical plates was charged with a mixture of 20.5% by weight of-n-butyl α-isocyanopropionate ($R_1$=n-butyl, $R_2$=methyl) and 79.5% by weight of tri-n-butylamine.

At 500 mbar top pressure and a bottom temperature of 165° C., 4-methyl-5-n-butoxyoxazole is withdrawn overhead as an azeotrope with tri-n-butylamine (90:10% by weight) having a boiling point of 158° C. High-boilers and tributylamine are withdrawn at the base of the column. The conversion was 98.4%, the selectivity 99%. The yield of 4-methyl-5-n-butoxyoxazole was 95% based on the n-butyl α-isocyanopropionate used.

The azeotrope was then separated in the same column at a top pressure of 10 mbar. The top product obtained is an azeotrope having the composition 4-methyl-5-n-butoxyoxazole:tri-n-butylamine=70:30 and the sidestream is pure 4-methyl-5-n-butoxyoxazole having a boiling point of 98° C. The distillation yield was 99% (40% of pure 4-methyl-5-n-butoxyoxazole and 60% of 4-methyl-5-n-butoxyoxazole as an azeotrope which was recycled into the first distillation). The pure 4-methyl-5-n-butoxyoxazole had a purity of 99.8%.

EXAMPLE 2

Continuous Preparation of 4-methyl-5-n-butoxyoxazole in a Dividing Wall Column Using a Solvent A continuously operated dividing wall column (4.8 m×64 mm) packed with 3×3 mm $V_2A$ Raschig rings and a dividing wall of height 2.4 m having 60 theoretical plates was charged with a mixture of 13.1% by weight of n-butyl α-isocyanopropionate ($R_1$=n-butyl, $R_2$=methyl), 32.2% by weight of monochlorobenzene and 50.1% by weight of tri-n-butylamine.

At 300 mbar top pressure and a bottom temperature of 169° C., monochlorobenzene having a boiling point of 90° C. is withdrawn overhead, and the sidestream is an azeotrope of 4-methyl-5-n-butoxyoxazole with tri-n-butylamine (88:12% by weight) having a transition temperature of 151° C. High-boilers and tributylamine are withdrawn at the base of the column. The conversion was 99.5%, the selectivity 99%. The yield of 4-methyl-5-n-butoxyoxazole was 94%, based on the n-butyl α-isocyanopropionate used.

The azeotrope was separated according to example 1.

EXAMPLE 3

Continuous Preparation of 4-methyl-5-n-butoxyoxazole in a Reaction Column Using a Solvent A column according to example 1 but without a dividing wall (see FIG. 1) was continuously charged via inlet (A) with a mixture of 20.6% by weight of chlorobenzene, 5.2% by weight of n-butyl α-isocyanopropionate ($R_1$=n-butyl, $R_2$=methyl) and 72.60% by weight of tris(2-ethylhexyl) amine.

At a top pressure of 300 mbar and a bottom temperature of 165° C., the solvent is withdrawn overhead (B). The 4-methyl-5-n-butoxyoxazole is obtained via sidestream takeoff (C) in a yield of 99%. The amine is discharged via the bottom takeoff (E).

EXAMPLE 4

Continuous Preparation of 4-methyl-5-n-butoxyoxazole in a Reaction Column

Example 3 is repeated, except that a mixture of 13.14% by weight of n-butyl α-isocyanopropionate and 86.86% by weight of tris(2-ethylhexyl)amine is continuously added via inlet (A).

At a top pressure of 400 mbar and a bottom temperature of 165° C. the 4-methyl-5-n-butoxyoxazole is withdrawn via the top takeoff (B) and the amine is discharged via the bottom takeoff (E). The yield of 4-methyl-5-n-butoxyoxazole is 98.8%.

EXAMPLE 5

Continuous Preparation of 4-methyl-5-isobutoxyoxazole in a Reaction Column

Example 3 is repeated, except that a mixture of 22.7% by weight of isobutyl α-isocyanopropionate and 77.3% by weight of N,N-dibutylaniline is added continuously via the inlet (A).

At a top pressure of 300 mbar and a bottom temperature of 160° C., the 4-methyl-5-isobutoxyoxazole is withdrawn at a temperature of 150° C. via the top takeoff (B). The amine is obtained via the sidestream D at 161° C. The yield of 4-methyl-5-isobutoxyoxazole is 91%.

EXAMPLE 6

Continuous Preparation of 4-methyl-5-n-butoxyoxazole in a Reaction Column

Example 5 is repeated except that a mixture of 11.8% by weight of n-butyl α-isocyanopropionate and 88.2% by weight of N,N-dibutylaniline is added continuously via the inlet (A). 4-Methyl-5-n-butoxyoxazole is obtained in a yield of 98.7% via the top takeoff B and the amine via the sidestream takeoff D.

EXAMPLE 7

Continuous Preparation of 4-methyl-5-butyloxyoxazole (MOX) in a Reaction Column Using n-butanol as a Cyclizing Assistant A continuously operated dividing wall column (4.8 m×64 mm) filled with 3×3 mm V₂A Raschig rings and a dividing wall of height 2.4 m having 60 theoretical plates was charged with a mixture of 30% by weight of n-butyl α-isocyanopropionate and 70% by weight of n-butanol via inlet (A).

At a top pressure of 300 mbar and a bottom temperature of 165° C., n-butanol is removed overhead. The column liquid phase is maintained at a constant level by using di-n-butyl phthalate as an intermediate boiler.

In the sidestream, 4-methyl-5-butyloxyoxazole (MOX) is obtained in 97% purity in a yield of 94%.

EXAMPLE 8

Continuous Preparation of 4-methyl-5-butyloxyoxazole (MOX) in a Reaction Column Using n-butyl Propionate as a Cyclizing Assistant The apparatus and experimental operation corresponds to example 7.

Example 7 is repeated, except that a mixture of 35% by weight of n-butyl α-isocyanopropionate and 65% by weight of n-butyl propionate are added continuously.

At a top pressure of 300 mbar and a bottom temperature of 165° C., n-butyl propionate is removed overhead. The column liquid phase is maintained at a constant level using di-n-butyl phthalate as an intermediate boiler.

In the sidestream, 4-methyl-5-butyloxyoxazole (MOX) is obtained in 95% purity in a yield of 92%.

EXAMPLE 9

Continuous Preparation of 4-methyl-5-butyloxyoxazole (MOX) in a Tubular Reactor and Subsequent Purification by Distillation in a Continuously Operated Column (tri-n-butylamine (TBA) Assistant)

The apparatus consisted of a 100 ml tubular reactor having a theoretical tank number of 120. The reactor was operated under pressure control at 5 bar. The feeding was effected under mass flow control in such a way that a residence time of 4 h was achieved.

The feed was a mixture of n-butyl α-isocyanopropionate (ICE) and tri-n-butylamine (TBA) in a molar ratio of 1:3 (mol of ICE/mol of TBA).

The effluent was collected. At a conversion of 54% of ICE and a selectivity of 92%, an MOX yield of 50% was obtained.

The reactor discharge was collected and distilled in a continuously operated column without a dividing wall (as in example 3).

The solution was passed in via the feed (nozzle A). At a pressure of 50 mbar and a bottom temperature from 80 to 90° C., the MoX/amine mixture was discharged overhead and ICE/amine withdrawn via a sidestream (in gaseous form) one plate above the bottom. The bottoms contained the high-boiling secondary components. It was discharged and disposed of.

The ICE/amine mixture was recycled into the reaction, the MOX top discharge purified to pure MOX.

Over the overall process, an ICE conversion of 100% was achieved. The selectivity toward MOX was 90%. The remainder were high-boilers which were discharged from the continuously operated distillation as the bottom product.

EXAMPLE 10

Continuous Pof 4-methyl-5-butyloxyoxazole (MOX) in a Tubular Reactor and Subsequent Purification by Distillation in a Continuously Operated Column (Diethylphenylamine Assistant)

In an apparatus as in example 9, the same conversion was effected using diethylphenylamine as assistant.

The discharge of the tubular reactor was collected. At a conversion of 58% ICE and a selectivity of 90%, an MOX yield of 53% was obtained.

Over the overall process, an ICE conversion of 100% was achieved. The selectivity toward MOX was 87%. The remainder were high-boilers which were discharged as the bottom product of the continuously operated distillation.

EXAMPLE 11

Continuous Preparation of 4-methyl-5-butyloxyoxazole (MOX) in a Tubular Reactor and Subsequent Purification by Distillation in a Continuously Operated Column (n-butanol Assistant)

In an apparatus as in example 9, the same conversion was effected using n-butanol as assistant.

The discharge of the tubular reactor was collected. At a conversion of 54% ICE and a selectivity of 93%, an MOX yield of 50% was obtained.

In this case, the column was operated with a dividing wall at 500 mbar. n-Butanol was withdrawn overhead. In the sidestream, MOX was obtained in a purity of 98%. Overhead, ICE was obtained with a purity of 95%.

The liquid phase was kept at a constant level with continuously metered-in dibutyl phthalate (5% by mass based on the feed). The overflow contained the high-boilers and was disposed of.

Over the overall process, an ICE yield of 100% was achieved. The selectivity toward MOX was 89%. The remainder were high-boilers which were discharged as the bottom product of the continuously operated distillation.

We claim:

1. A process for continuously preparing 5-alkoxy-substituted oxazoles of the formula I

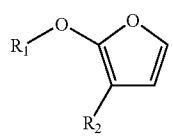

I where
   $R^1$ is an unsubstituted or substituted $C_1$–$C_6$-alkyl radical and
   $R^2$ is hydrogen or an unsubstituted or substituted $C_1$–$C_6$-alkyl radical, which comprises
converting continuously added α-isocyanoalkanoate esters of the formula II

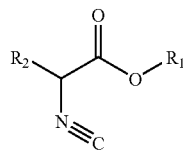

II in the presence of continuously added cyclizing assistants selected from the group consisting of bases, alcohols and esters,
at temperatures above 80° C.
in a reaction column
to the 5-alkoxy-substituted oxazoles of the formula I, and continuously removing the 5-alkoxy-substituted oxazoles of the formula I from the reaction mixture by rectification, wherein the rectification parameters are set in such a way that
   A the α-isocyanoalkanoate esters of the formula II are converted to the 5-alkoxy-substituted oxazoles of the formula I on internals in the reaction column and, if present, in a liquid phase of the reaction column,
   B the 5-alkoxy-substituted oxazoles of the formula I resuling from the conversion are continuously removed with a top stream or sidestream of the reaction column and
   C the assistant and any high-boilers resulting from the conversion are removed continuously and independently of each other with a bottom stream or sidestream of the reaction column.

2. The process of claim 1, wherein the conversion is carried out in the presence of an inert solvent and the reaction parameters are set in such a way that
   A the α-isocyanoalkanoate esters of the formula II are converted to the 5-alkoxy-substituted oxazoles of the formula I on the internals and, if present, in the liquid phase of the reaction column,
   B1 when the solvent has a higher boiling point than the 5-alkoxy-substituted oxazoles of the formula I resulting from the conversion, the 5-alkoxy-substituted oxazoles of the formula I are continuously removed with the top stream and the solvent is continuously removed via, the sidestream or bottom stream of the reaction column,
   B2 when the solvent has a lower boiling point than the 5-alkoxy-substituted oxazoles of the formula I resulting from the conversion, the 5-alkoxy-substituted oxazoles of the formula I are continuously removed with a sidestream and the solvent is continuously removed with the top stream of the reaction column, and
   C the assistant and any high-boilers resulting from the conversion are removed continuously and independently of each other with the bottom stream or sidestream of the reaction column.

3. The process of claim 1, wherein the reaction column used is a dividing wall column.

4. The process of claim 1, wherein, when the assistant forms an azeotrope with the 5-alkoxy-substituted oxazoles of the formula I, the top pressure of the column is set in such a way that the fraction of the assistant in the azeotrope in the top stream is as low as possible.

5. The process of claim 1, wherein the top pressure of the column is set to from 5 to 800 mbar and the resulting bottom pressure, which depends on the type of column used and, if used, the type of column internals, is from 10 mbar to atmospheric pressure.

6. A process for prepering pyridoxine derivatives of the formula IX

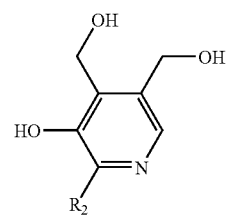

IX where
   $R_2$ is hydrogen or an unsubstituted or substituted ($C_1$–$C_6$-alkyl radical, which comprises converting amino acids of the formula III

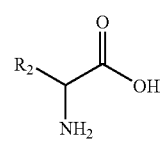

III to ammo esters of the formula IV,

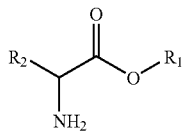

IV where
$R_1$ is an unsubstituted or substituted $C_1$–$C_6$-alkyl radical,
converting the latter into formamido esters of the formula V,

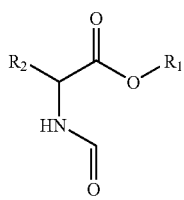

V converting the latter into α-isocyanoalkanoate esters of the formula II,

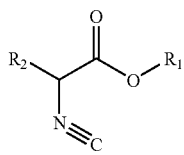

II converting the latter by the process of claim 1 to 5-alkoxy-substituted oxazoles of the formula I

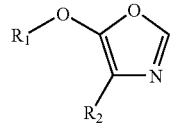

I reacting the latter with protected diols of the formula VI

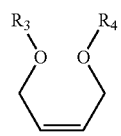

VI where
$R_3$ and $R_4$ independently or $R_3$ and $R_4$ together are a protecting group of the hydroxy function,
to give the Diels-Alder adducts of the formula VII

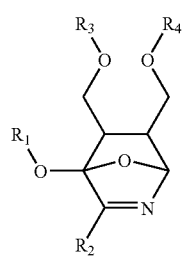

VII and converting the latter by acid treatment and detachment of the protecting group to the pyridoxine derivatives of the formula IX.

* * * * *